United States Patent [19]

Braglia et al.

[11] Patent Number: 5,010,253

[45] Date of Patent: Apr. 23, 1991

[54] DETECTION SYSTEM FOR CATHODOLUMINESCENCE ANALYSIS

[75] Inventors: Marco Braglia, Turin; Roberto DeFranceschi, Vinovo; Paolo Montangero, Turin, all of Italy

[73] Assignee: SIP - Societa Italiana per L-Esercizio Delle Telecomunicazioni P.A., Turin, Italy

[21] Appl. No.: 445,412

[22] Filed: Dec. 4, 1989

[30] Foreign Application Priority Data

Dec. 16, 1988 [IT] Italy .................. 68115 A/88

[51] Int. Cl.$^5$ ............................................. H01J 37/09
[52] U.S. Cl. .................................. 250/399; 250/503.1; 250/505.1
[58] Field of Search ............... 250/307, 310, 397, 399, 250/503.1, 505.1

[56] References Cited

U.S. PATENT DOCUMENTS

| | | | |
|---|---|---|---|
| 3,146,347 | 8/1964 | Ziegler | 250/310 |
| 3,864,570 | 2/1975 | Zingaro | 250/310 |
| 4,121,010 | 10/1978 | Lasky et al. | 250/483.1 |
| 4,218,617 | 8/1980 | Cazaux | 250/397 |
| 4,806,772 | 2/1989 | Lindmayer | 250/484.1 B |

OTHER PUBLICATIONS

J. M. Reau et al., "Alkali Fluoride Containing Fluorozirconate Glasses . . . ", (Journal of Solid State Chemistry, 60, 159-164, 1985).

B. Carette et al., "Ionic Conduction of Sulphide-Based Glasses . . . ", (Glass Technology, vol. 24, No. 3-Jun. 1983).

J. Marek et al., "A Novel Scheme for Detection of Defects in . . . Semiconductors . . . ", (Journal of Electrochemical Society, Jun. 1985).

Matusita et al., "Anionic Conduction . . .", (Technological University . . . , Nagaoka, Japan).

Primary Examiner—Bruce C. Anderson
Attorney, Agent, or Firm—Herbert Dubno

[57] ABSTRACT

Detection system for cathodoluminescence analysis apparatus, wherein a screen is placed between the sample to be analyzed and the detector to intercept the electrons backscattered by the sample towards the detector. The screen is a plate of a glass which is transparent in a wide spectral interval, has a rather high conductivity, and does not present cathodoluminescence effects.

7 Claims, 1 Drawing Sheet

DETECTION SYSTEM FOR CATHODOLUMINESCENCE ANALYSIS

FIELD OF THE INVENTION

The present invention relates to apparatus for material analysis by cathodoluminescence and more particularly concerns a detection system for such apparatus.

BACKGROUND OF THE INVENTION

It is known that a sample of suitable material, bombarded by electrons, returns part of the received energy by photon emission. By collecting said photons by a suitable detector it is possible to build up an image of the analyzed area, thus obtaining information on the material properties. When making measurements by that technique it is necessary to collect and send to the detector as many photons as possible. The simplest solution would be to place the detector as close as possible to the sample emitting surface, but under these conditions the surface of the conventional glass screens protecting the detectors becomes charged by backscattered electrons. This charging generates an electric field which disturbs electron beam scanning. If the detector is placed relatively far from the sample, beyond the reach of the electrons, the signal emitted from the detector can be too low to permit a precise interpretation. Whatever the detector position, mirrors can be used to increase the collection solid angle, but such mirrors generally prevent the microscope use at low magnifications and are difficult to use (ie. constitute an encumbrance in the analysis chamber, make it necessary to center the sample with respect to the mirror, etc.).

The problem of simultaneously ensuring a good collection efficiency and good screening against backscattered electrons can be solved by placing the detector near the sample and placing therebetween a screen which is transparent to photons and thick enough to retain the electrons, which does not give rise to luminescence when struck by backscattered electrons and, finally, which does not give rise to electron charging of its surface, to avoid creating an electrical field capable of disturbing the scanning beam. To meet these requirements, it has been proposed to make a glass screen coated with a very thin metal conductive coating. This solution is described by J. Marek, R. Geiss, L. M. Glassman and M. P. Scott in the paper entitled "A Novel Scheme for Detection of Defects in III-V Semiconductors by Cathodoluminescence", Glass Technology, Vol. 24, No. 3, June 1983.

This known solution has a number of disadvantages. The metal coating increases absorption, consequently reducing the level of the detector output signal, what renders the measurement more sensitive to noise and requires more powerful, and hence more expensive, amplification systems. Additional work is required to fabricate the coating, and this also increases the costs. Finally, conventional oxide glasses present a fair transparency in a spectral region which, in the infrared, does not extend beyond 2.4 $\mu$m.

OBJECT OF THE INVENTION

The object of the present invention is to provide a screen which wholly meets the requirements above and which does not give rise to problems with signal power, does not require additional work and has good transparency over a wide spectral region.

SUMMARY OF THE INVENTION

The present invention provides a detection system for apparatus for material analysis by cathodoluminescence, wherein a material sample is scanned by an electron beam and photons generated by electron bombardment are collected by a detector, and wherein a screen is located between the sample and the detector to intercept electrons backscattered towards the detector by the material or electrons transmitted towards the detector. According to the invention, the screen consists of a plate of a glass selected from fluoride glasses, chalcogenide glasses, and Ag-based glasses.

Preferably the fluoride glasses used are fluorozirconate or fluorohafnate glasses or glasses with a high content of lithium fluoride.

The use of these glasses satisfactorily eliminates the drawbacks described above. In fact, these glasses have good transparency in a wide wavelength range, which can reach the mid-infrared spectral region, up to about 8 $\mu$m. Besides, the conductivity of such glasses under the temperature conditions to which they can be exposed during a cathodoluminescence measurement (substantially ambient temperature) is some orders of magnitude higher than that of ordinary glasses used for conventional screens, so that the metal coating usually used on earlier screen can be dispensed with.

BRIEF DESCRIPTION OF THE DRAWING

Other characteristics of the invention will result from the following description, with reference to the accompanying drawing in which.

SPECIFIC DESCRIPTION

Figure 1:
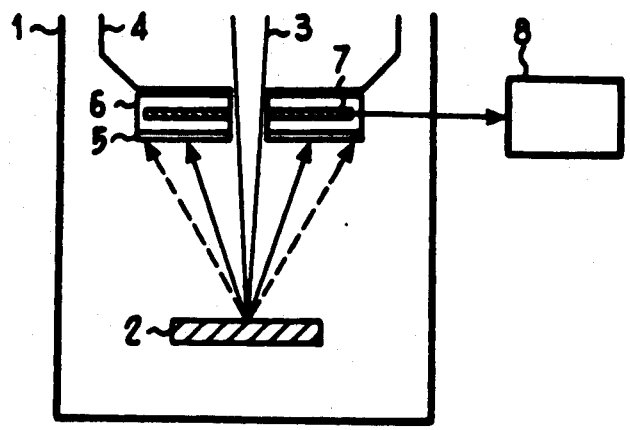
FIG. 1 is a diagrammatic cross sectional view illustrating the invention.

In the drawing, the chamber 1, of a scanning electron microscope receives a sample 2 for analysis. The sample is mounted on a conventional object holder which allows the area to be analyzed to be brought under the scanning electron beam 3. The holder is not shown, since it is that of a conventional scanning electron microscope and is not affected by the present invention. The microscope objective 4 focuses beam 3 on sample 2. The solid angle of collection of photons emitted by the sample as a consequence of electron bombardment is shown by dashed lines.

A plate 5 of a glass with relatively high conductivity is placed in the trajectory of the photons emitted by the sample, which plate acts as a screen for intercepting backscattered electrons, is transparent to photons and does not present cathodoluminescence effects. Plate 5 is mounted inside a housing 6 also containing detector 7, e.g. a silicon detector as described in the above mentioned paper by J. Marek and al. Detector 7 is connected to electronic circuits 8 which process the signals supplied by the detector as required by the concerned analysis. The processing is are known to those skilled in the art and is not affected by the invention. Plate 5 will obviously be grounded to avoid electron charging of the glass.

As shown in FIG. 1, plate 5 and detector 7 can be located substantially in correspondence with lens 4, coaxially with scanning beam 3, and can have an axial hole to allow the beam passage.

Figure 2:
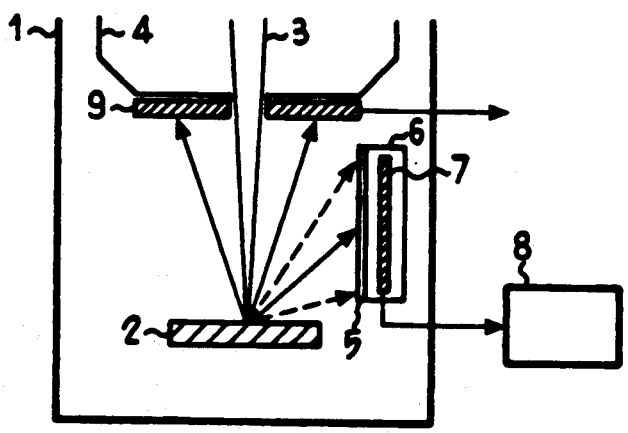
FIG. 2 is a similar view of another embodiment.

In the diagram of FIG. 2, screen 5 and detector 7 are arranged so as to collect photons comprised within an emission cone whose axis is inclined with respect to the incident beam axis. By this arrangement, the solid angle which can be observed by detector 7 is narrower than in the preceding case. Backscattered electrons can also be detected by an additional detector 9.

Figure 3:
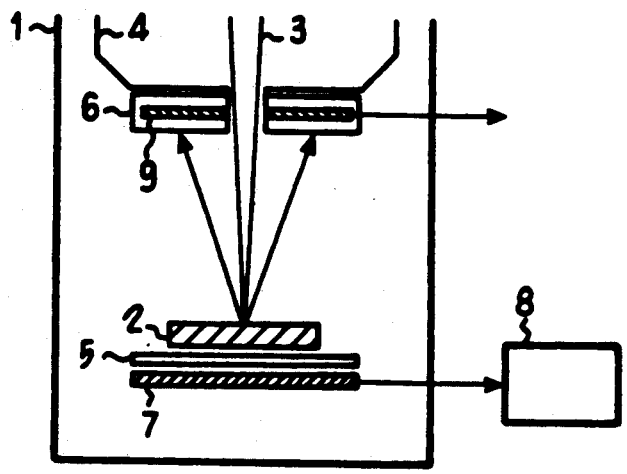
FIG. 3 is a view of a third embodiment.

In the diagram of FIG. 3, relative to transmissive cathodoluminescence, screen 5 supports sample 2 and prevents primary beam electrons from arriving onto detector 7; also in this case backscattered electrons can be detected by detector 9.

Screen 5 can be made from fluoride or chalcogenide glasses. Both these types of glasses exhibit a good transparency in a wide range of wavelengths (up to mid-infrared). In addition, many fluoride or chalcogenide glass compositions have high electric conductivity. For instance, a number of chalcogenide glasses exhibit, at ambient temperature, a conductivity of the order of $10^{-2} \text{ohm}^{-1} \text{cm}^{-1}$ (see B. Carette et al. "Ionic conduction of sulphide-based glasses in the systems M2S-GeS2-MI (M=Li, Ag)). Fluoride glasses with a high LiF content exhibit a conductivity (at 175° C.) of the order of $10^{-4} \text{ohm}^{-1} \text{cm}^{-1}$, as reported by Reau et al. in the paper entitled "Alkali Fluoride Containing Fluorozirconate Glasses: Electrical properties and NMR investigations", Journal of Solid State Chemistry, Vol. 50 (1985), pages 159-164; several fluorozirconate glasses (containing or not containing LiF) have conductivities (at 150°-175° C.) in the range $10^{-4}$ to $10^{-6}$ $\text{ohm}^{-1} \text{cm}^{-1}$, as reported in the cited paper by Reau et al. and in the paper "Anionic conduction in various fluoride glasses" by K. Matusita et al., Journal of Non Crystalline Solids, Vol. 95-96, pages 945 to 952. Even though conductivity of these glasses at ambient temperature is lower, nevertheless it is considerably higher than that of conventional oxide glasses, which at ambient temperature exhibit maximum conductivity of the order of $10^{-10} \text{ohm}^{-1} \text{cm}^{-1}$.

It is to be noted that in applications in which transparency to infrared is not required, Ag-based glasses can be used, namely glasses made from mixtures of AgI and silver oxysalts, which have a conductivity of $10^{-2}$ $\text{ohm}^{-1} \text{cm}^{-1}$.

The screen can have a thickness of a fraction of millimeter.

We claim:

1. A detection system for material analysis by cathodoluminescence, comprising:
   means for directing a beam of electrons onto a sample of a material to be analyzed whereby said sample generated photons characteristic of said material;
   a detector positioned proximal to said sample for receiving photons generated by said sample; and
   a photon-passing electron-blocking screen disposed between said sample and said detector to intercept electrons from said sample and prevent impingement of electrons from said sample on said detector, said screen being constituted of a plate of a glass selected from the group which consists of fluoride glasses, chalcogenide glasses and Ag-based glasses.

2. The detection system defined in claim 1 wherein said plate is composed of a fluoride glass of a high lithium fluoride content.

3. The detection system defined in claim 1 wherein said plate is a support for said sample.

4. A detection system for material analysis by cathodoluminescence, comprising:
   means for directing a beam of electrons onto a sample of a material to be analyzed whereby said sample generated photons characteristic of said material;
   a detector positioned proximal to said sample for receiving photons generated by said sample; and
   a photon-passing electron-blocking screen disposed between said sample and said detector to intercept electrons from said sample and prevent impingement of electrons from said sample on said detector, said screen being constituted of a plate of a glass selected from the group which consists of fluoride glasses, selected from the group which consists of fluorozirconate and fluorohafnate glasses and Ag-based glasses containing a mixture of AgI and silver oxysalts.

5. The detection system defined in claim 4 wherein said plate is composed of a fluoride glass selected from the group which consists of fluorozirconate and fluorohafnate glasses.

6. The detection system defined in claim 4 wherein said plate is composed of an Ag-based glass containing a mixture of AgI and silver oxysalts.

7. The detection system defined in claim 4 wherein said plate is a support for said sample.